United States Patent

Dougherty et al.

[11] Patent Number: 5,728,138
[45] Date of Patent: Mar. 17, 1998

[54] CARDIAC DEFIBRILLATOR WITH MULTI-PHASE FERROELECTRIC/ANTIFERROELECTRIC CAPACITOR

[75] Inventors: Joseph P. Dougherty, State College, Pa.; Kamau Wa Gachigi, Narita, Japan; Thomas R. Shrout, Port Matilda, Pa.; Sei-Joo Jang; Clive A. Randall, both of State College, Pa.; Philip M. Pruna, Canandaigua, N.Y.

[73] Assignee: The Penn State Research Foundation, University Park, Pa.

[21] Appl. No.: 688,883

[22] Filed: Jul. 31, 1996

[51] Int. Cl.[6] .................................................. A61N 1/39
[52] U.S. Cl. .................................................. 607/5; 361/313
[58] Field of Search .......................... 607/5; 361/313, 361/320, 321.4, 321.5; 501/134, 135

[56] References Cited

U.S. PATENT DOCUMENTS

5,163,427  11/1992  Keimel .

*Primary Examiner*—William E. Kamm
*Assistant Examiner*—Kennedy J. Schaetzle
*Attorney, Agent, or Firm*—Thomas J. Monahan

[57] ABSTRACT

A cardiac defibrillator includes a multilayer capacitor with a plurality of conductive electrodes and interspersed dielectric layers, each dielectric layer composed of constituents which cause it to exhibit an antiferroelectric phase. The constituents of each dielectric layer are such as to cause each layer to exhibit plural ferroelectric phases. The defibrillator includes a charging circuit for applying to the capacitor an electric field across each dielectric layer which causes a transition thereof through the plural ferroelectric phases. PLZT is the preferred dielectric material, at constituent values which cause the material to lie within the antiferroelectric phase and to exhibit plural ferroelectric phases.

14 Claims, 7 Drawing Sheets

PLZT 6/100/0

PLZT 6/100/0
FIG.2

PLZT x/100/0
FIG.6

PLZT x/97.5/2.5
FIG.7

CARDIAC DEFIBRILLATOR WITH MULTI-PHASE FERROELECTRIC/ ANTIFERROELECTRIC CAPACITOR

RELATED PATENT APPLICATION

This invention is related to the invention disclosed and claimed in U.S. patent application Ser. No. 08/423,500, entitled "Cardiac Defibrillator with High Energy Storage Antiferroelectric Capacitor," now U.S. Pat. No. 5,545,184.

FIELD OF THE INVENTION

This invention relates to cardiac defibrillators and, more particularly, to an implantable cardiac defibrillator employing a high energy density multi-phase, switching, antiferroelectric capacitor.

BACKGROUND OF THE INVENTION

Cardiac defibrillators are implanted in patients suffering from potentially lethal arrhythmias. An implantable defibrillator includes circuitry which monitors cardiac activity and decides, based upon the cardiac activity, whether an application is required of defibrillation energy to the heart muscle. If an arrhythmia is detected, pacing or shock therapy may be used to terminate the arrhythmia.

Cardioversion and defibrillation require that a high voltage shock be delivered to the heart muscle. Upon determining a need for such shock treatment, the defibrillator charges a capacitor to a high level, which charge is then delivered as a shock to the heart muscle. The voltage applied across the heart muscle may be as high as 800 volts and the energy applied to the heart muscle is delivered within a very short time period (e.g. 5 milliseconds).

Early work by Schuder, et al. ("Transthoracic Ventricular Defibrillation with Triangular and Trapezoidal Waveforms", *Circulation Research*, Vol. XIX, October 1966, pp. 689–694) demonstrated that the pulse shape influences the efficacy of defibrillation. The most commonly held theory on the optimization of defibrillation pulse shape is the average current hypothesis, which is an adaptation of simple cardiac stimulation theory. This general theory states that the efficacy of defibrillation is solely dependent upon the average current of the pulse and the duration of the pulse. This theory implies that other parameters of the pulse are not critical. A recent review of this theory is provided in the article by Mark W. Kroll ("A Minimal Model of the Monophasic Defibrillation Pulse", *Pacing and Clinical Electrophysiology*, Vol. 16, Part I, April, 1993, pp. 769–777). A more complete review of the influence of pulse shape is provided by W. A. Tacker and Leslie A. Geddes in *Electrical Defibrillation* (CRC Press, Inc., Boca Raton, Fla., 1980 (Chapter 4)). Based on this theory and the results of these and other published experiments, defibrillation with rectangular pulse has been shown to require less peak current and less energy than is required for any other monophasic pulse shapes. In general, these studies indicate that energy stored at high electrical potential is more effective at defibrillating a heart than the same amount of energy stored at low electrical potential. Further, it has been shown that long, low amplitude tails on the pulse are detrimental to defibrillation.

As capacitors in a defibrillator must today store up to 40 joules, the size they occupy is generally large and they are difficult to package in a small implantable device. Multilayer ceramic capacitors have not been commercialized for high energy storage applications, even though some exhibit very large dielectric constants. Such high voltage multilayer ceramic capacitors, in large sizes, have been expensive specialty items and their total energy per unit volume is not nearly as high as in electrolytic capacitors. Recently, fabrication technologies for multilayer ceramic capacitors have improved significantly, permitting both substantially higher energy densities and lower costs.

To achieve acceptable performance for a capacitor in a defibrillator, its energy discharge capacitors must be able, for example, to withstand an applied voltage of approximately 800 volts, exhibit a capacitance of approximately 50 to 150 microfarads and occupy a volume of less than 20 cubic centimeters. An energy storage capacity up to 40 joules is required. Ferroelectric ceramics, while having extremely high dielectric constant values at low electric fields, exhibit a significant fall off in capacitance with increasing levels of applied electric field. In fact, at high field values, the exhibited capacitance can be as little as 10% of that at low dc field values. That is, conventional ferroelectric capacitors store a larger portion of their total charge at low voltage as compared with linear dielectric capacitors which maintain a constant capacitance independent of applied voltage. Lastly, ferroelectric materials can also show a substantial hysteresis loss in the charge/discharge characteristic.

A class of non-linear, antipolar ceramic materials, termed antiferroelectrics, exhibits increasing dielectric constant as electric fields are increased. With further increase in the electric field antiferroelectrics undergo a phase transition to a ferroelectric phase and then show a similar decrease in dielectric constant as is shown by conventional ferroelectrics.

U.S. patent application, Ser. No. 08/423,500, referred to above, describes an improved cardiac defibrillator which incorporates a multilayer capacitor with a plurality of conductive electrodes and interspersed dielectric layers, each dielectric layer composed of constituents which cause the dielectric layer to exhibit antiferroelectric characteristics. The defibrillator includes a charging circuit for applying to the capacitor an electric field across each dielectric layer that is approximately $E_f$, where $E_f$ is a field value that causes the dielectric layer to transition to a ferroelectric phase. $E_f$ is selected, together with each dielectric layer thickness, such that the ferroelectric transition occurs near the maximum desired voltage of an output pulse. The preferred dielectric material disclosed by Dougherty et al. comprises lead, lanthanum, zirconium and titanium, all at constituent values which cause the resulting ceramic material to lie within the antiferroelectric region. When a voltage is applied across the multilayer capacitor (and its antiferroelectric dielectric layers) which causes each layer to transition to its ferroelectric phase, upon electrical discharge, an extraordinarily large energy output is achieved in the upper voltage reaches of the charge/discharge characteristic.

Notwithstanding the considerable improvement in discharge characteristics of the capacitive structures disclosed by Dougherty et al., still greater energy storage capacitors are desired to enable further size reductions of the implantable device.

Accordingly, it is an object of this invention to provide an improved, implantable cardiac defibrillator.

It is another object of this invention to provide an improved storage capacitor for use in an implantable cardiac defibrillator.

It is yet another object of this invention to provide an improved capacitor for an implantable cardiac defibrillator wherein the capacitor occupies less volume than prior art capacitors.

SUMMARY OF THE INVENTION

A cardiac defibrillator incorporating the invention hereof includes a multilayer capacitor with a plurality of conductive electrodes and interspersed dielectric layers, each dielectric layer composed of constituents which cause it to exhibit an antiferroelectric phase. The constituents of each dielectric layer are such as to cause each layer to exhibit plural ferroelectric phases. The defibrillator includes a charging circuit for applying to the capacitor an electric field across each dielectric layer which causes a transition thereof through the plural ferroelectric phases. PLZT is the preferred dielectric material, at constituent values which cause the material to lie within the antiferroelectric phase and to exhibit plural ferroelectric phases.

DETAILED DESCRIPTION OF THE INVENTION

Requirements placed upon a capacitor operating in an implantable cardiac defibrillator are (1) that it have an effective operating voltage for the particular electrode system applied to the heart, (2) that it have the capacity to store up to 40 joules, (3) that its discharge rate enable the release of a majority of its stored energy within a 1 to 20 millisecond time period, and (4) that it occupies as small a volume as possible. As indicated above, antiferroelectric materials have not been favored for capacitor applications due to their poor energy storage characteristics at low voltages. However, applicants have determined that a class of antiferroelectric materials exhibits a particular characteristic which matches the energy storage requirements of a cardiac defibrillator.

Figure 1:
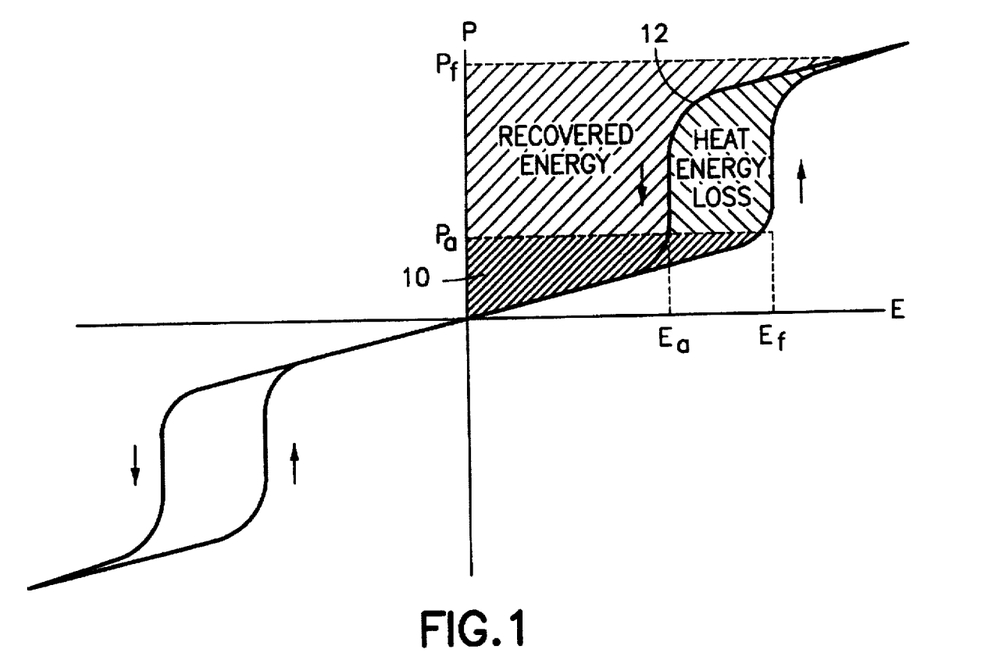
FIG. 1 is a plot of polarization P versus electric field E for an antiferroelectric material.

Antiferroelectric crystalline materials exhibit structural phase changes, nonlinearities in dielectric permittivity, and other properties similar to ferroelectrics. However, antiferroelectric materials have zero net switchable dipole moment per unit cell, and consequently they exhibit no macroscopic polarization hysteresis in their low signal region. Because of the lack of macroscopic remnant polarization, so long as an antiferroelectric dielectric is maintained in its low voltage region, it experiences very little hysteresis loss. However, as shown in FIG. 1, antiferroelectric dielectrics have at least one ferroelectric phase which can be induced by application of an electric field of sufficient magnitude. The threshold field required to induce a ferroelectric phase is designated $E_f$. If, after field-inducing the ferroelectric phase, the magnitude of the applied electric field is transition occurs is designated $E_a$. reduced, the dielectric material returns to its initial antiferroelectric phase. The field at which the latter transition occurs is designated $E_a$.

In FIG. 1, electric field E is plotted against polarization P for an antiferroelectric material. During lower levels of applied electric field, the polarization is substantially linear with applied electric field. The shaded area 10 is proportional to the energy stored when the applied electric field is $E_f$. At the $E_f$ transition, (antiferroelectric-to-ferroelectric), the dielectric constant of the material increases significantly, thus facilitating a large energy storage (i.e. polarization) capability with only a small increase in applied electric field—a phenomenon not seen in linear capacitors. As a result, the amount of energy stored increases rapidly until the polarization reaches point $P_f$ where the energy storage characteristic becomes linear again. Upon discharge, the return curve 12 exhibits a hysteretic effect with the energy within the hysteresis region being lost as heat. Nevertheless, it is to be noted that the energy from $P_a$ to $P_f$ is recovered while the dielectric maintains a constant voltage and until the discharge curve reaches the ferroelectric-to-antiferroelectric transition field $E_a$.

In a capacitor, the applied voltages which cause electric fields $E_a$ and $E_f$ can be tailored by appropriate dimensioning of the dielectric layer thicknesses. It is generally desirable to have $E_a$ as close as possible to $E_f$ to increase the electric field to discharge efficiency and to reduce heat losses during a charge/discharge cycle. In a wide range of antiferroelectrics, $E_f$ can be set so that the voltage at which the transition occurs can be tailored to the specific needs of the patient. Thus, for a capacitor charged to a polarization level of about $P_f$, upon discharge, most stored energy has been released when $P_a$ is reached. This energy release occurs at a high electric potential and is the feature which has been found to match the requirements of an implantable cardiac defibrillator.

In the aforementioned, copending patent application Ser. No. 08/423,500 of Dougherty et al., a class of PLZT ceramics is identified which exhibits polarization/electric field characteristics somewhat similar to that shown in FIG. 1, i.e. a transition from an antiferroelectric phase to a single ferroelectric phase. Later work has occurred with a class of PLZT ceramics (with and without titanium) which exhibit plural ferroelectric phase transitions as electric field values are increased. Substantially improved energy storage characteristics have been found that are directly applicable to a defibrillator application.

Figure 2:
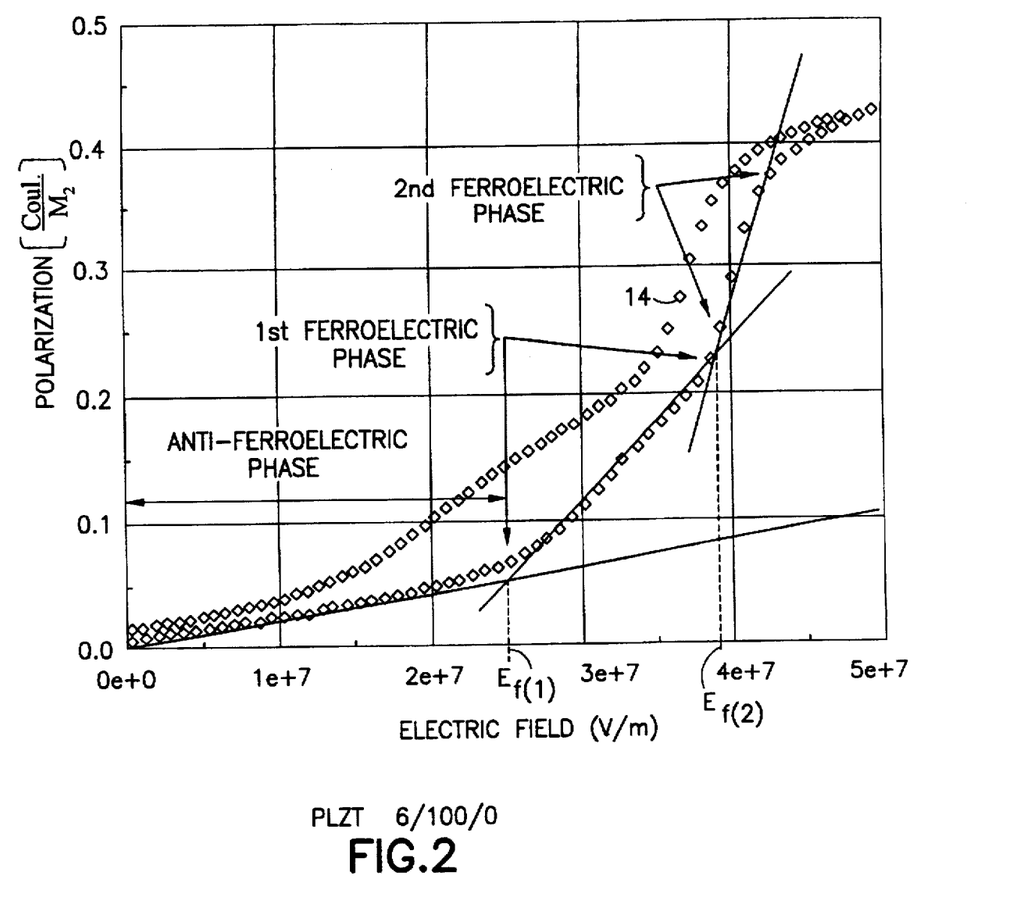
FIG. 2 is a plot of polarization versus electric field for an antiferroelectric material exhibiting plural ferroelectric phases.

FIG. 2 shows a plot of polarization vs. electric field for a 6/100/0 PLZT composition. (As known to those skilled in the art, the "6" value equates to the molar percent of lanthanum with respect to lead, the "100" to the molar percent of zirconium with respect to titanium and the "0" to the molar percent of titanium with respect to zirconium). A transition from the antiferroelectric phase to a first ferroelectric phase occurs at $E_{f(1)}$ (i.e. approximately $2.5 \times 10^7$ V/m). This transition is apparent from the discontinuity in the hysteresis plot at $E_{f1}$. The first ferroelectric phase remains until $E_{f(2)}$ (i.e. approximately $3.9 \times 10^7$ V/m), at which point a transition occurs to a second ferroelectric phase. Thereafter, at approximately $4.2 \times 10^7$ V/m, the material transitions from the second ferroelectric phase to saturation. It is to be understood that the term "phase", as used herein, is not to be limited to a change of crystal structure in a material, but is to be interpreted as encompassing any change in the polarization/electric field behavior of a material.

It has been determined that each phase transition of the material allows a now higher level of polarization (charge per unit of volume) to be accumulated, thus increasing, substantially, the stored energy. Each square of the plot of FIG. 2 equates to one Joule per $cm^3$ of stored energy. Thus, by counting the squares (and parts of squares) to the left of a hysteresis curve's return plot (i.e. through data points 14), it can be seen that the resulting energy storage of PLZT 6/100/0 is approximately 12 Joules per $cm^3$. By contrast, the energy storage of the best PLZT material identified in the aforementioned Dougherty et al. patent application (i.e. PLZT 4/95/5) was approximately 7.5 Joules per $cm^3$.

Accordingly, in any circuit in which a multitransition PLZT material is used as a capacitor dielectric layer, the layer design and applied voltage should assure that the applied electric field across each layer is at least equal to or greater than the field which causes the material to transition to the ferroelectric phase that exists just prior to saturation— assuring storage of the maximum amount of energy.

Figure 3:
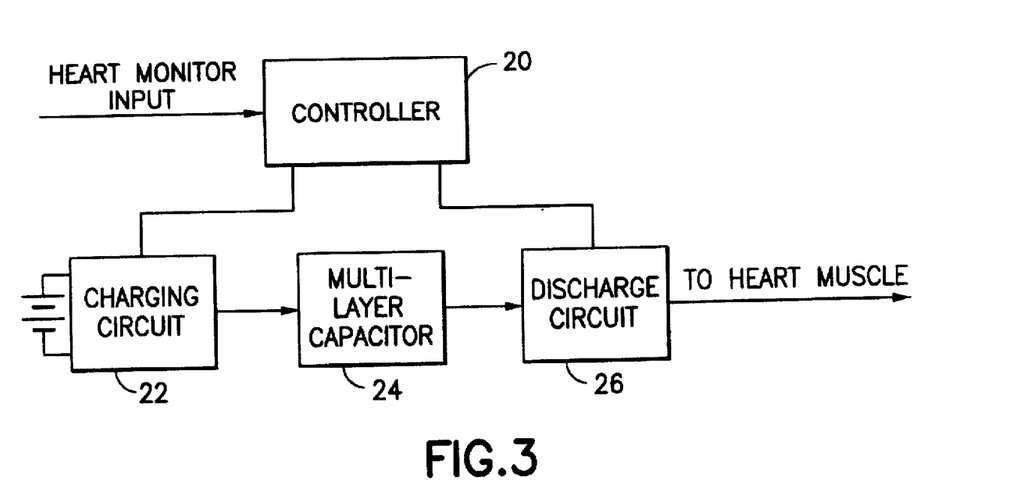
FIG. 3 is a high level block diagram of an implantable cardiac defibrillator.

Referring to FIG. 3, a block diagram is illustrated of an implantable cardiac defibrillator that employs a multilayer antiferroelectric ceramic capacitor. A controller 20 monitors the heart action and, upon determining that an tachyarrhythmic condition is occurring, causes a charging circuit 22 to charge multilayer capacitor 24 to a high voltage. While certain heart arrhythmias only require a small applied voltage to correct the arrhythmia, should a ventricular fibrillation occur, a high energy voltage pulse must be applied to the heart muscle to cause a desired conversion back to a sinus rhythm. At such time, controller 20 causes charging circuit 22 to charge multilayer capacitor 24 up to a programmed setting as high as its maximum (e.g., 700–800 volts). When the charge cycle is complete, controller 20 enables discharge circuit 26 to discharge the energy to the cardiac muscle. For further details of a cardiac defibrillator see U.S. Pat. No. 5,163,427 to Keimel, the disclosure of which is incorporated herein by reference.

With reference to FIG. 2, the voltage applied by charging circuit 22 to multilayer capacitor 24 should preferably cause the electric field to equal or exceed the value $E_{f(1)}$, and preferably $E_{f(2)}$, for the particular antiferroelectric dielectric employed in capacitor 24 to take advantage of the large energy storage capability at this value. In some cases, it may be desired that the field be between $E_{f(1)}$ and $E_{f(2)}$ to produce a level of polarization with lesser amounts of substrate stress.

Following the work of Schuder et al. (1966) and Kroll (1993), it has been shown that "for effective ventricular defibrillation, that long, low amplitude tails on shocks are detrimental". Therefore, the discharge pulses, which typically follow an exponential decay $I = I_o e^{-t/RC}$, are usually truncated at approximately $t=RC$, where $R=50$ $\Omega$ is the resistance in the chest-heart circuit, C is the capacitance and $I_o$ is the initial charging current $I_o = V_{max}/R$. It can thus be seen that only the electrical energy stored at the upper ⅔ range of voltage is preferably used in defibrillation.

Figure 4:
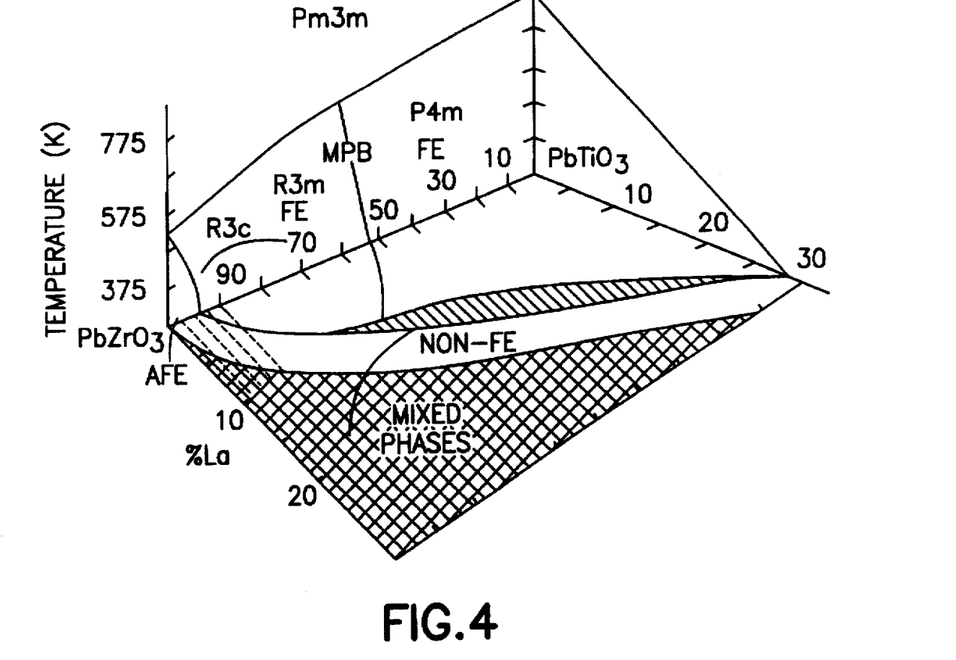
FIG. 4 is a phase diagram for various PLZT compositions.

Referring now to FIG. 4, a PLZT phase diagram is illustrated. The phase diagram shown in FIG. 3 is for various compositions of lead, lanthanum, zirconates and titanates (PLZT). Lanthanum substitutes for the lead ions in the structure and tends to break up the translational invariance in the crystal lattice. The phase diagram indicates that for PZT ($PbTiO_3$-$PbZrO_3$ solid solutions) compositions occur at ~5% $PbZrO_3$ and greater, while ferroelectric phases begin at lower $PbZrO_3$ content. On addition of lanthanum (up to ~10%), the antiferroelectric phase stability is widened to include compositions with up to ~70% $PbTiO_3$, at temperatures of between room temperature and 40° C. As the lanthanum content increases further, the phase diagram indicates that a region of mixed phases is present. Research indicates that the hysteresis loops become increasingly narrow as the lanthanum content increases. As such it is seen that a variety of high field behavior is available in the PLZT system.

In FIG. 4, the following abbreviations are employed:
FE=ferroelectric
AFE=antiferroelectric
Pm3m=cubic phase (above Tc)
P4mm=tetragonal ferroelectric phase
MPB=morphotropic phase boundary
R3m=ferroelectric rhombohedral phase
R3c=different ferroelectric rhombohedral phase The dots at the left of the diagram illustrate PLZT compositions investigated.

Figure 5:
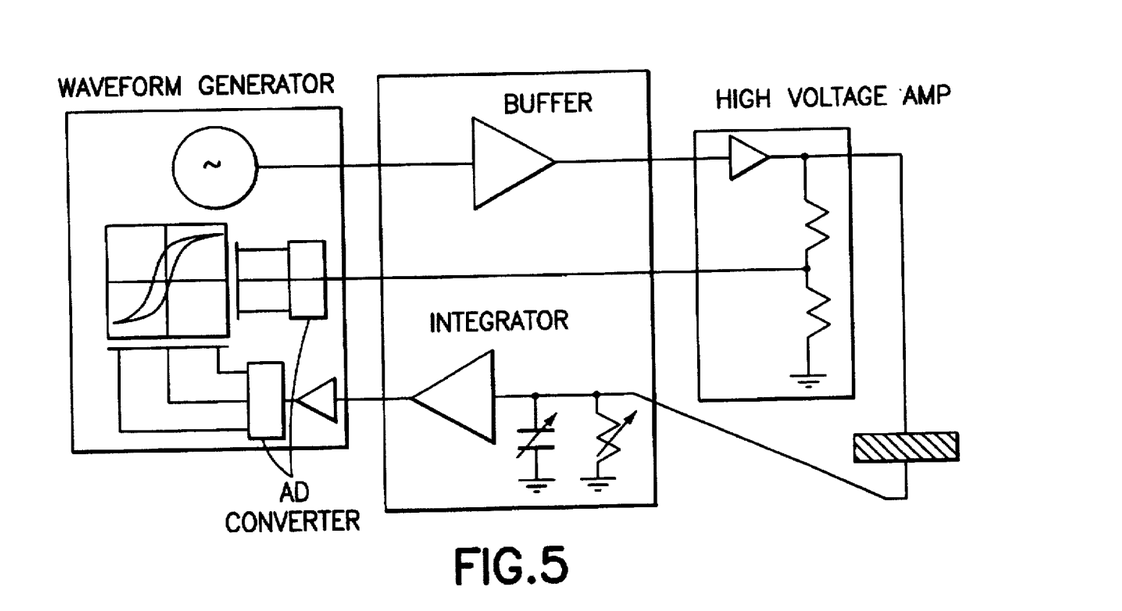
FIG. 5 is a circuit diagram of a test circuit used to obtain the data plotted in the Figs.

High field measurements were made using the Sawyer-Tower circuit shown in FIG. 5. Measurements were made at 0.2 Hz using both unidirectional and bidirectional voltage application with a triangular wave form. Ceramic disc samples used had been polished down to thicknesses of ~80 um to 160 um. Sputtered gold electrodes were employed allowing an uncoated ring on the periphery of the disk so as to prevent current flashover. The Sawyer-Tower circuit requires current to be sourced at a set voltage ramp rate. Because of the power limitations of the amplifiers, low frequency measurements are required, particularly at the point at which the abrupt switching occurs, placing considerable current demands on the system. Because of this, energy density measurements must be made by discharging the stored charge through a resistive load. This notwithstanding, hysteresis loops provide key information on the switching fields in the materials.

Figure 6:
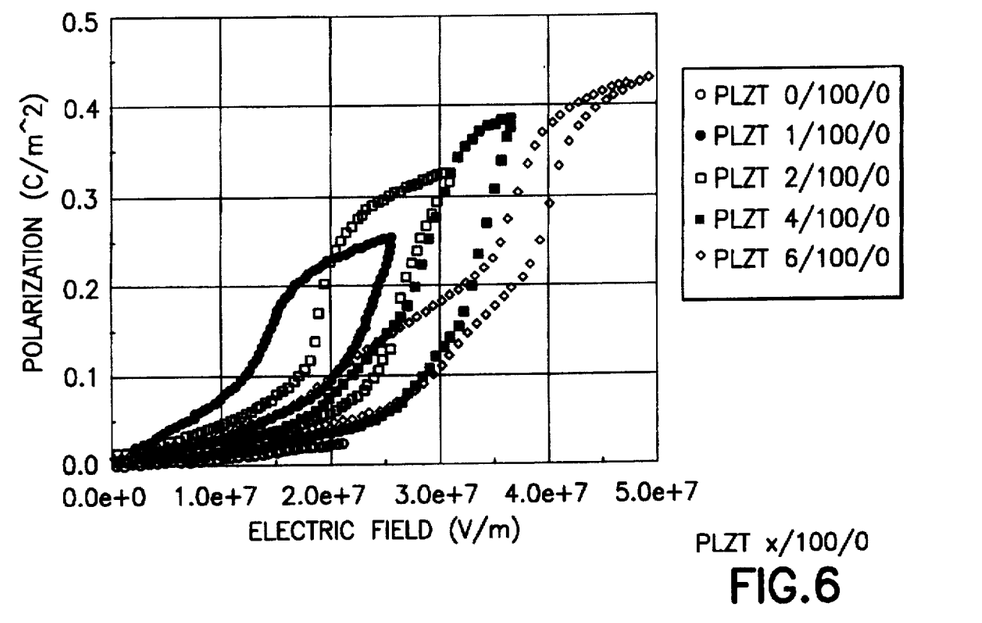
FIG. 6 is a plot of polarization versus electric field for the PLZT family x/100/0.

As will be seen from the plots of FIGS. 6–13, many PLZT compositions were investigated and their hysteresis characteristics plotted. In FIG. 6 it can be seen that the PLZT 6/100/0 composition yielded the best energy storage when the lanthanum content was varied. Note the plural ferroelectric transitions in both PLZT 4/100/0 and 6/100/0.

Figure 7:
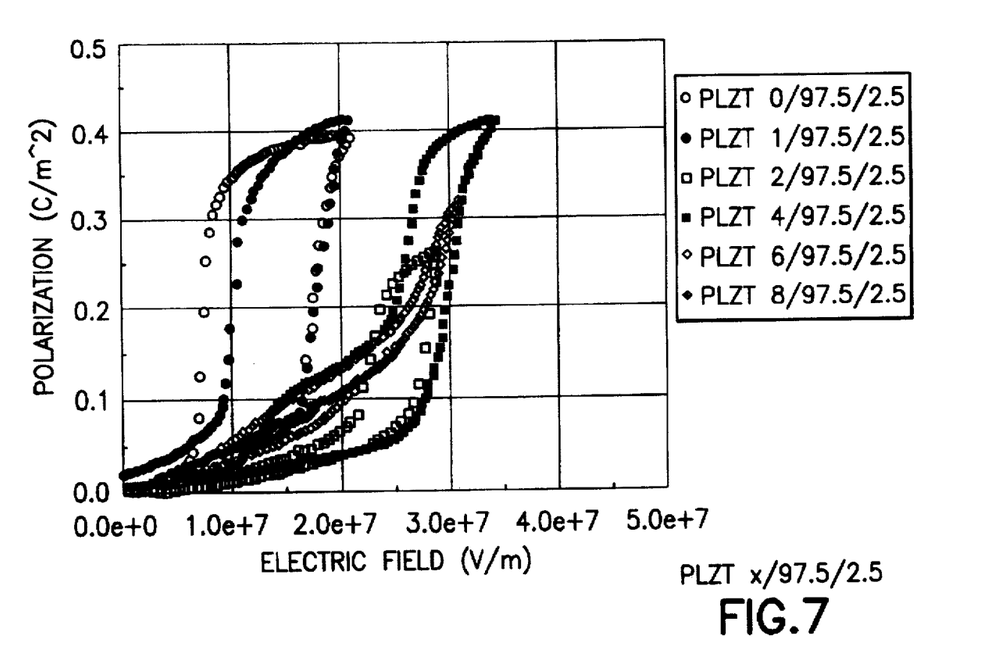
FIG. 7 is a plot of polarization versus electric field for the PLZT family x/97.5/2.5.
Figure 8:
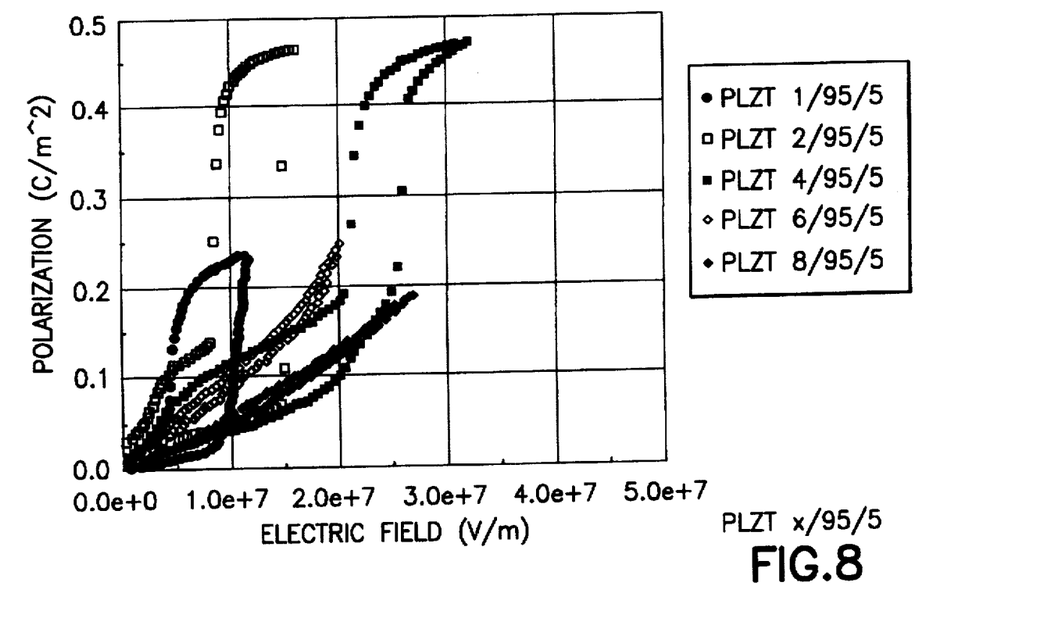
FIG. 8 is a plot of polarization versus electric field for the PLZT family x/95/5.
Figure 9:
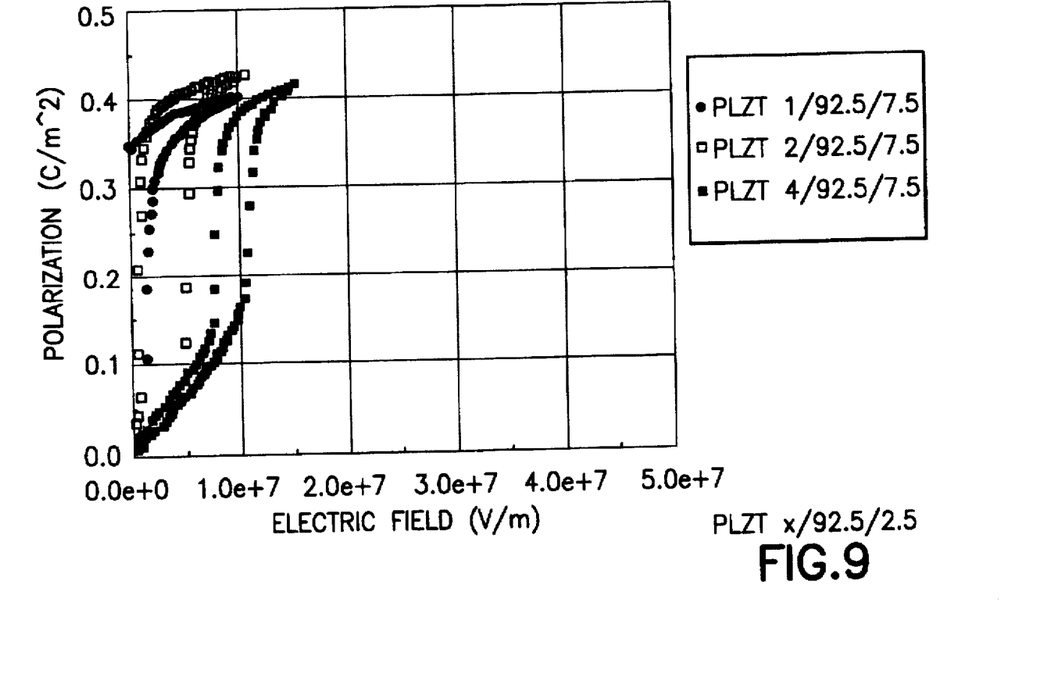
FIG. 9 is a plot of polarization versus electric field for the PLZT family x/92.5/2.5.

FIG. 7 illustrates the results when the lanthanum content was varied with a 2.5 percent titanium inclusion in the PLZT composition. PLZT 4/97.5/2.5 exhibited the best energy storage characteristic. In FIG. 8, the titanium value was increased to 5% and the tests repeated. PLZT 4/95/5 exhibited plural ferroelectric transitions and the best energy storage characteristic. When the titanium value was further increased to 7.5% (see FIG. 9), plural ferroelectric phases were not seen and the energy storage characteristics were poor by comparison. The 1/92.5/7.5 and 2/92.5/7.5 materials appear to act like normal ferroelectrics.

Figure 10:
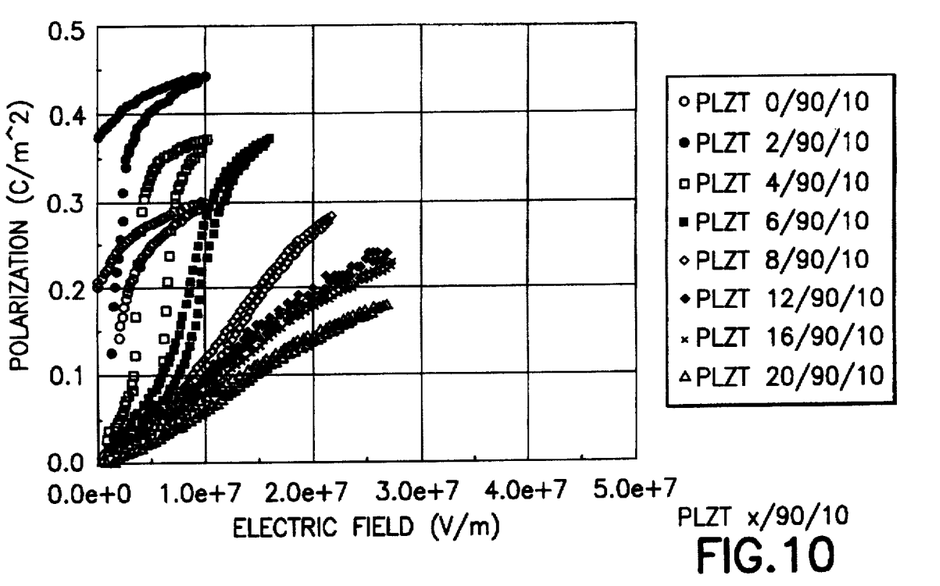
FIG. 10 is a plot of polarization versus electric field for PLZT family x/90/10.
Figure 11:
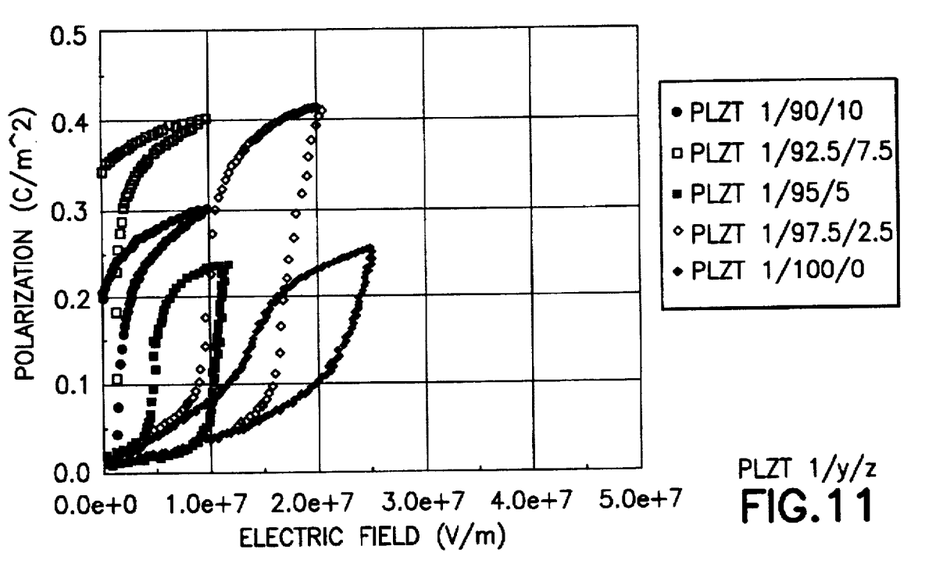
FIG. 11 is a plot of polarization versus electric field for the PLZT family 1/y/z.

In FIG. 10, the titanium percentage was increased to 10% and the lanthanum percentage varied. Here again, the energy storage characteristics were poor by comparison. In FIG. 11, the lanthanum percentage was maintained constant at 1% and the zirconium and titanium percentages were varied. No plural ferroelectric phases transitions were observed.

Figure 12:
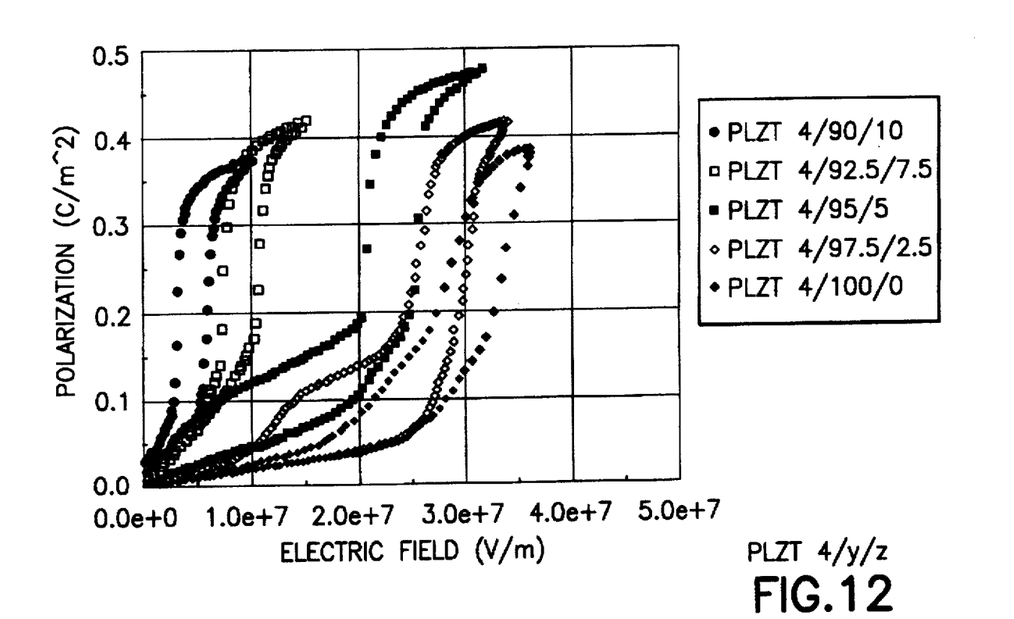
FIG. 12 is a plot of polarization versus electric field for PLZT family 4/y/z.

In FIG. 12, however, when the lanthanum content was increased to 4%, PLZT compositions 4/95/5; 4/97.5/2.5 and 4/100/0 all exhibited plural ferroelectric transitions and substantially improved energy storage characteristics. Note that the 4/95/5 PLZT composition was found to be most preferred in the previous Dougherty et al. application Ser. No. 08/423,500, but it was not (at that time) understood that the existence of plural ferroelectric phases gave rise to a further enhanced energy storage capability.

Figure 13:
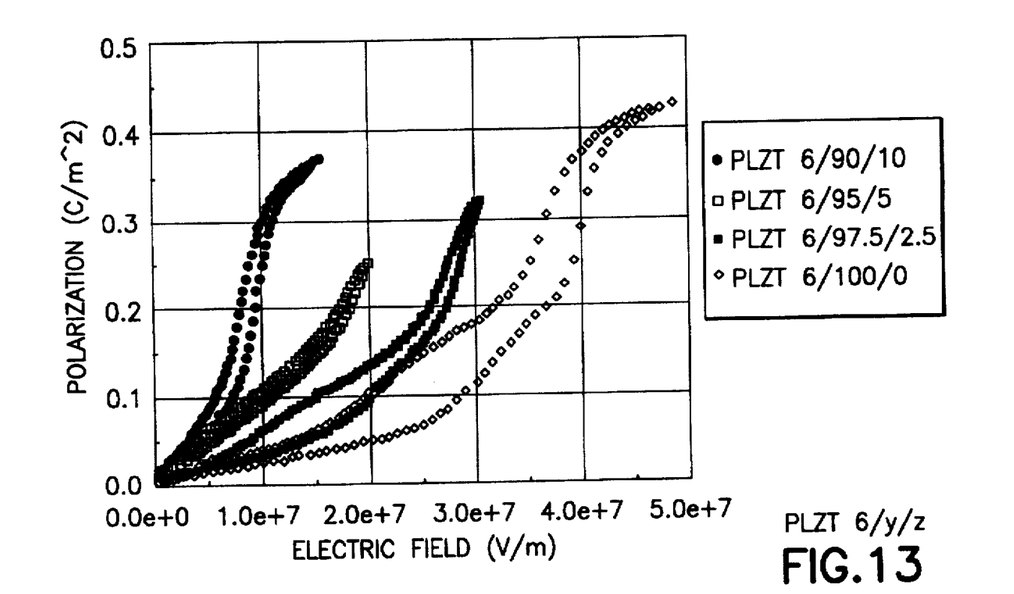
FIG. 13 is a plot of polarization versus electric field for the PLZT family 6/y/z.

In FIG. 13, the lanthanum content was increased to 6% and the zirconium and titanium percentages were varied. PLZT 6/100/0 was found superior in energy storage characteristics.

As indicated above, a capacitor for use with an implantable defibrillator has stringent imposed requirements which include an operating voltage up to 800 volts, a capacitance of approximately 50 to 150 microfarads, and a volume of approximately 20 cubic centimeters (or less). Assuming a voltage value of 800 volts and that the breakdown strength of the capacitor's dielectric is 80 volts per micron, to achieve an operating voltage rating of 800 volts, the thickness of the dielectric must at least equal 10 microns. Using the capacitance and volume specifications, the minimum dielectric constant K for a linear capacitor can be calculated as follows:

$$K = \frac{C \cdot t^2}{\epsilon_o(At)} \quad (1)$$

where

At=volume ($m^3$)

$\epsilon_o = 8.854 \times 10^{-12}$ Farads/meter

A=capacitor surface area ($m^2$)

t=thickness of the dielectric (m)

C=capacitance (Farads)

The precise design of a nonlinear capacitor will, of course, depend upon the average K value for the specifically chosen antiferroelectric, as calculated over the total voltage and electric field range.

In summary, a variety of PLZT compositions have been tested and found applicable for use as dielectric materials in capacitors used with defibrillators. While a number of PLZT compositions which fall within the antiferroelectric region have been tested, other compositions which exhibit antiferroelectric properties will also exhibit the characteristic of high energy release at upper voltage reaches of the charge/discharge characteristic. As has been shown by Schuder et al. and Kroll, the energy released at higher voltages, which makes the current pulse more closely resemble a square wave, has been shown experimentally to be more effective for defibrillation. For instance, some PbSnZrTi and PbBaLaZrTi materials exhibit antiferroelectric characteristics. In any case, it is critical that the applied voltage across the antiferroelectric material cause the material to transition through its plural ferroelectric phase states. It is these transitions which enable an extraordinarily large discharge of energy to occur at upper voltage reaches of the charge/discharge characteristic.

While it can be seen from the above data that certain PLZT compositions are particularly useful in the defibrillator application, a wide variation of constituents in the ultimate PLZT composition is also within the preferred range. Thus the PLZT composition may exhibit a La molar percentage extending from approximately 1 to 10, a Zr molar percentage of approximately from 90 to 100 and a Ti molar percentage of approximately from 0 to 10. The most preferred compositions are PLZT's 6/100/0; 4/100/0; and 4/97.5/2.5. It has also been determined that Ca can be substituted for the La inclusion, over the same ranges of Zi and Ti, and within the same ranges as recited for La.

It is evident in FIGS. 11–13 that the switching fields increase as the $PbZrO_3$ content increases, because this increases the antiferroelectric phase stability of the material. These plots also indicate that for higher Zr/Ti ratios, increasing the lanthanum content increases both the switching field and, in some cases, the maximum polarization. Increasing the lanthanum content for constant Zr/Ti ratios generally increases the switching field as well. It further appears that the lead zirconate composition doped with 6% of lanthanum (PLZT 6/100/0) offers exceptional properties with a switching field on discharge of the order of 350 kV/cm and maximum polarization of ~0.4 $C/m^2$.

It should be understood that the foregoing description is only illustrative of the invention. Various alternatives and modifications can be devised by those skilled in the art without departing from the invention. For instance, barium can be substituted for lead in the PLZT compositions. Barium substitution should be limited to 10 mole %. Accordingly, the present invention is intended to embrace all such alternatives, modifications and variances which fall within the scope of the appended claims.

What is claimed is:

1. Apparatus for applying a high energy, short duration electrical pulse to an output, said apparatus comprising:

capacitor means for energy storage, said capacitor means comprising plural dielectric layers, each layer composed of constituents which exhibit both an antiferroelectric phase and plural ferroelectric phases, in dependence upon an applied electric field;

charging circuit means for applying to said capacitor means a voltage to cause energy storage therein, said voltage causing an electric field at least equal to $E_f$ to appear across said dielectric layers, where $E_f$ is a field value which causes said dielectric layers to transition from said antiferroelectric phase through said plural ferroelectric phases; and discharge means for applying energy stored in said capacitor means to said output.

2. The apparatus as recited in claim 1, wherein each said dielectric layer comprises lead, lanthanum, zirconium and titanium (PLZT) constituents.

3. The apparatus as recited in claim 2, wherein the lanthanum, zirconium and titanium constituents are present in the PLZT in molar percentages as follows:

La: from approximately 1 to 10,

Zr: from approximately 90 to 100 and

Ti: from approximately 0 to 10.

4. The apparatus as recited in claim 2, wherein the lanthanum and zirconium constituents are present in molar percentages of approximately 6 and 100, respectively.

5. The apparatus as recited in claim 2, wherein the lanthanum and zirconium constituents are present in molar percentages of approximately 4 and 100, respectively.

6. The apparatus as recited in claim 2, wherein the lanthanum, zirconium and titanium constituents are present in molar percentages approximately 4, 97.5 and 2.5, respectively.

7. The apparatus as recited in claim 1, wherein each said dielectric layer comprises lead, calcium, zirconium and titanium constituents.

8. The apparatus as recited in claim 7, wherein the calcium, zirconium and titanium constituents are present in molar percentages as follows:

Ca: from approximately 1 to 10,

Zr: from approximately 90 to 100 and

Ti: from approximately 0 to 10.

9. The apparatus as recited in claim 7, wherein the calcium and zirconium constituents are present in molar percentages of approximately 6 and 100, respectively.

10. The apparatus as recited in claim 7, wherein the calcium and zirconium constituents are present in molar percentages of approximately 4 and 100, respectively.

11. The apparatus as recited in claim 7, wherein the calcium, zirconium and titanium constituents are present in molar percentages approximately 4, 97.5 and 2.5, respectively.

12. An apparatus as recited in claim 1, wherein each said dielectric layer comprises barium, lanthanum, zirconium and titanium constituents.

13. An apparatus as recited in claim 1, wherein each said dielectric layer comprises barium, calcium, zirconium and titanium constituents.

14. The apparatus as recited in claim 1 wherein said output of said discharge means is adapted to apply said energy to a heart muscle.

* * * * *